United States Patent
Davis et al.

(10) Patent No.: US 6,620,352 B1
(45) Date of Patent: Sep. 16, 2003

(54) AUTOMATED MATERIAL DISTRIBUTION CONTROL FOR STRETCH BLOW MOLDED ARTICLES

(75) Inventors: Craig Davis, Atlanta, GA (US); Spencer Minton, Marietta, GA (US); Eddy Roberts, Douglasville, GA (US)

(73) Assignee: Ball Corporation, Broomfield, CO (US)

( * ) Notice: Subject to any disclaimer, the term of this patent is extended or adjusted under 35 U.S.C. 154(b) by 544 days.

(21) Appl. No.: 09/626,992

(22) Filed: Jul. 27, 2000

(51) Int. Cl.[7] .................. B29C 49/12; B29C 49/68; B29C 49/78
(52) U.S. Cl. ............... 264/40.4; 264/40.6; 264/521; 264/532; 264/535; 425/140; 425/143; 425/169; 425/215; 425/526; 425/529
(58) Field of Search ................. 264/40.4, 40.6, 264/509, 521, 532, 535; 425/140, 143, 169, 215, 526, 529

(56) References Cited

U.S. PATENT DOCUMENTS

| | | |
|---|---|---|
| 3,934,743 A | 1/1976 | McChesney et al. |
| 3,956,441 A | 5/1976 | Uhlig |
| 4,044,086 A | 8/1977 | McChesney et al. |
| 4,117,050 A | 9/1978 | Appel et al. |
| 4,131,666 A | 12/1978 | Agrawal et al. |
| 4,151,249 A | 4/1979 | Lee |
| 4,170,622 A | 10/1979 | Uhlig |
| 4,287,150 A | 9/1981 | Gendron |
| 4,307,137 A | 12/1981 | Ota et al. |
| 4,320,083 A | 3/1982 | Jakobsen |
| 4,323,341 A | 4/1982 | Valyi |
| 4,359,165 A | 11/1982 | Jakobsen |
| 4,420,670 A | 12/1983 | Croswell et al. ......... 219/10.81 |
| 4,490,612 A | 12/1984 | Törmälä |
| 4,564,497 A | 1/1986 | Ota et al. |
| 4,571,173 A | 2/1986 | Chang et al. |
| 4,587,075 A | 5/1986 | Butcher et al. |
| 4,785,950 A | 11/1988 | Miller et al. |
| 4,927,679 A | 5/1990 | Beck |
| 4,997,692 A | 3/1991 | Yoshino |

(List continued on next page.)

FOREIGN PATENT DOCUMENTS

| | | | |
|---|---|---|---|
| JP | 05309723 | 11/1993 | ........... B29C/49/08 |
| WO | WO 9706429 A1 * | 2/1997 | ........... G01N/21/90 |

*Primary Examiner*—Robert Davis
(74) *Attorney, Agent, or Firm*—Brinks Hofer Gilson & Lione

(57) ABSTRACT

A method for inspecting the material distribution of a sequence of stretch blow molded containers or other articles in a continuous production process, by providing injection molded parisons, each parison having at least one indicator, typically two or more indicators, for detecting material distribution at a predetermined position along the axial extent of the parison. Each of the parisons is subjected to a heating stage in the continuous production process, generally by exposure to infrared heating. Each heated parison is then subjected to a blow molding process, which can be a stretch blow molding process, so that each material distribution indicator is transformed to a corresponding position along the axial extent of the blow molded article. A detector is positioned to detect the location of each indicator on each blow molded article from a given mold in the production process. A computation is then made to determine for each blow molded article a material distribution outcome or profile based on the detected locations of each indicator. This information on material distribution is them matched to a prescribed profile for the particular container design and any discrepancy beyond some preset tolerance value is employed to reject the out of tolerance item from the production line, and to modify a step of the manufacturing process such as the infrared heating pattern.

32 Claims, 8 Drawing Sheets

U.S. PATENT DOCUMENTS

| | | |
|---|---|---|
| 5,049,750 A | 9/1991 | Hoshino et al. ............ 250/341 |
| 5,057,267 A | 10/1991 | Seizert et al. |
| 5,066,222 A | 11/1991 | Roos et al. |
| 5,101,990 A | 4/1992 | Krishnakumar et al. |
| 5,102,588 A | 4/1992 | Feuerherm |
| 5,116,565 A | 5/1992 | Yoshino |
| 5,139,406 A * | 8/1992 | Hoshino et al. ............ 425/140 |
| 5,259,716 A | 11/1993 | Hoshino et al. ............ 414/225 |
| 5,312,572 A | 5/1994 | Horwege |
| 5,437,702 A * | 8/1995 | Burns et al. ............... 65/29.12 |
| 5,443,868 A | 8/1995 | Oda et al. |
| 5,591,462 A * | 1/1997 | Darling et al. .............. 425/173 |
| 5,688,466 A * | 11/1997 | Mitchell et al. ............ 264/458 |
| 5,902,526 A | 5/1999 | Davis et al. |
| 5,917,328 A | 6/1999 | Dimmick et al. |
| 6,473,169 B1 * | 10/2002 | Dawley et al. .......... 356/239.4 |

* cited by examiner

AUTOMATED MATERIAL DISTRIBUTION CONTROL FOR STRETCH BLOW MOLDED ARTICLES

BACKGROUND OF THE INVENTION

1. Field of the Invention

The present invention generally relates to the field of blow molding articles from plastic parisons, and more particularly concerns methods and systems for producing stretch blow molded articles formed of polymeric resin and having consistent physical dimensions.

2. Description of the Prior Art

Providing consistent physical dimensions, including consistent material distribution, has been a chronic problem in production of blow molded articles, such as those articles formed from polymeric resins such as polyethylene terephthalate (PET). Difficulties in achieving consistent physical dimensions, such as material distribution, has led to problems in assuring acceptably high quality of such articles. In addition, difficulties arising from the lack of uniform physical dimensions can exist across various production platforms and between production facilities seeking to produce substantially identical blow molded articles. Consistent physical dimensions such as material distribution are very important for end performance characteristics of blow molded articles, e.g., stretch blow molded containers, such as burst strength, top load strength, thermal deformation resistance, and stress cracking resistance.

Current material distribution analysis techniques directed to already formed blow molded articles are time consuming, relatively crude in that such techniques provide only gross material distributions, and, in addition, do not lend themselves to automated inspection. One current analysis technique for material distribution is the so-called section weighing method, where, for instance, portions of a stretch blow molded article such as a base, label panel, and shoulder, are cut away from each other and individually weighed to ascertain whether these sections weigh within prescribe tolerances. Despite the availability of the section weighing method, and while this method is adequate for gross determination of overall material distribution of the sections, the section weighing method cannot account for variability within the section, although variability within a section of a blow molded article has been frequently observed in both laboratory and production environments. Further, the section weighing method is necessarily destructive of the article and can only be performed on a very small number of the articles, while most (perhaps as much as 99.9%) of the articles manufactured by a particular line are not inspected at all for material distribution. Therefore, the section weighing method can only be used to indirectly determine whether the material distribution of a stretch blow molded article which has not been cut and weighed but was made using the production parameters of a section weighed article is within acceptable tolerances. Further, there is no easy method of integration of the results of such testing back into the manufacturing process to achieve articles having more uniform or desirable parameters.

Consequently, there exists a need in the art for methods and systems for directly and non-destructively assuring consistent physical dimensions such as material distribution for stretch blow molded articles, in order to produce stretch blow molded articles of consistent quality across various production platforms and between different production facilities. Preferably such systems can be applied to a substantial portion, if not all, of the containers manufactured in a given production line so that product quality can be maintained to better standards.

Our prior patent, namely, U.S. Pat. No. 5,902,526, disclosed a method for inspecting blow molded articles on a continuous or substantially continuous basis, wherein the parisons employed in the blow molding process included a plurality of first markers formed at preselected position on the parison exterior surface. The first markers were generally in the form of light circumferential lines disposed generally planarly and parallel to each other, each line forming a complete outwardly projecting annulus on the exterior surface of the parison. The product is formed by placing such a parison in a blow mold having sections defined generally by smooth interior surfaces, but having a plurality of second differentially dimensioned portions, each second differentially dimensioned portion disposed at a predetermined location on stretch blow mold interior surface. The location of each second differentially dimensioned portion was generally selected to correspond with the optimum location of one of the first markers when the parison was transformed by the blow molding process to conform to the interior of the blow mold. The second differentially dimensioned portions could be disposed on the blow mold interior surface in any of a variety of configurations and orientations, such as where the individual second differentially dimensioned portions are formed of small or large differentially dimensioned segments disposed planarly or non-planarly, or as raised or depressed impressions on the blow mold interior surface, or by modified surface finish of blow mold interior surface.

In a finished article formed in accordance with U.S. Pat. No. 5,902,526, the relative position of first markers with respect to the corresponding, proximately disposed second markers indicates whether at least one dimension is within the preselected range. For example, the thickness dimension of a profile of the article may be determined to be within a preselected range of thicknesses by ascertaining whether the distance between each first marker and a corresponding second marker is less than a preselected distance. The marker can be formed to define tolerance bands or zones. Upon blowing the parison with the first markers within such a mold produces an article having second markers defining a tolerance zone or band, and including a plurality of first markers in close relation to the plurality of corresponding tolerance zones. The relative position of the first markers with respect to corresponding, proximate tolerance zones indicates whether at least one dimension is within a preselected range. Where the first markers lie within corresponding tolerance zones, the at least one dimension will be within a preselected range. However, if a first marker lies outside the corresponding tolerance, then the at least one dimension is not within a preselected range.

Inherent in the process of U.S. Pat. No. 5,902,526 is the need to form both the first marker on the parison and the second marker upon blow molding the finished article, followed by comparing their relative location. While such overlapping or closely proximate markings can be formed in a manner to be detected by individual visual inspection, the use of such a system of markers in connection with any automatic inspection system has proven to be elusive if not impossible. U.S. Pat. No. 4,131,666 also employed a surface grid marking technique followed by visual examination to determine the distribution of plastic in a finished container, but did not suggest any manner of converting the visual inspection to one that might be automated.

The control of variations in dimensions of finished articles through modifications in process parameters is taught generally by U.S. Pat. Nos. 3,934,743 and 4,044,086. Other patents, e.g., U.S. Pat. Nos. 3,956,441; 4,307,137; and 4,564,497, have disclosed structures included on the surface of parisons to achieve decorative effects on the finished articles. Still other patents, e.g., U.S. Pat. Nos. 4,151,249; 4,320,083; 4,359,165; 4,785,950; 4,927,679; 4,997,692; 5,101,990; 5,116,565 and 5,312,572, have disclosed structures included on the surface of parisons to achieve structural effects in the finished articles. U.S. Pat. No. 4,117,050 discloses the longitudinal thermal profiling of a parison to control wall thickness distribution in blow molded articles, but does not discuss any scheme for automated inspection of the resulting articles. U.S. Pat. Nos. 4,571,173 and 5,066,222 disclose schemes by which the temperature of a parison is heated in a non-uniform manner as a function of time to achieve the optimum heat profile for blow molding, but again there is no discussion of any scheme for automated inspection of the resulting articles.

There continues to be a need for a control system that can be employed in a continuous production process, wherein the system relies at least in part on some direct or indirect measurement of one or more selected criteria of the finished blow molded articles, to control or modify the manufacturing conditions so that the material distribution for a sequence of blow molded articles, such as stretch blow molded containers, remains within some defined range of normal values.

SUMMARY OF THE INVENTION

In order to aid in the understanding of the present invention, it can be stated in essentially summary form that it is directed to a method and system for the production of blow molded articles, such as stretch blow molded containers, from injection molded parisons, having well controlled physical dimensions so that optimum articles are produced consistently. The method and systems of the present invention include non-destructive, direct measurement of the molded articles to ensure consistent and controlled physical dimensions for such molded articles, providing an accuracy level for physical dimensions and resultant quality of such molded articles that far exceeds that available from current methods and apparatus.

More specifically, the present invention involves a method for inspecting the material distribution of a sequence of stretch blow molded containers in a continuous production process, by providing injection molded parisons, each parison having at least one indicator for detecting material distribution at a predetermined position along the axial extent of the parison. Each of the parisons is subjected to a heating stage in the continuous production process, generally by exposure to infrared heating. Each heated parison is then subjected to a blow molding process, which can be a stretch blow molding process, so that each material distribution indicator is transformed to a corresponding position along the axial extent of the blow molded container or other article. A detector is positioned to detect the location of each indicator on each blow molded container from a given mold in the production process. A computation is then made to determine for each blow molded container a material distribution outcome or profile based on the detected locations of each indicator. This information on material distribution is them matched to a prescribed profile for the particular container design and, if any discrepancy beyond some preset tolerance value is detected, a mechanism is employed to reject the out of tolerance item from the production line. Further, a modification is made to a step of the manufacturing process based on the nature of the discrepancy such as the infrared heating pattern employed.

When the inspection method of the present invention is employed in a manufacturing process using a plurality of blow molds in a continuously repeated cycle, there is a need to compare the information on material distribution taken from articles produced in the same blow mold so that variations between blow mold are screened from the data. This is achieved by providing a scribe in a selected blow mold of the plurality of blow molds capable of molding a mark on each respective container blow molded in the selected blow. The mark identifying the marked container can then be detected and each subsequent unmarked container in the continuous cycle, if produced in serial fashion, can be related to other specific blow molds used in the process. The material distribution data for each of the marked containers can be correlated, recorded, and/or employed to modify a step of the manufacturing process such as the infrared heating pattern. The variation in the determined material distribution data for any of the subsequent unmarked blow molded containers in the cycle can be employed to address a specific problem associated with the specific blow mold in which the container was made.

In some processes, it may be unnecessary or inappropriate to adjust or modify the manufacturing process in response to the material distribution data for each of the marked containers. Instead, samples from the sequence of stretch blow molded containers can be selected on any desired basis or frequency, and the sample containers employed to calculate an average material distribution outcome for the samples based on the determined material distribution outcome for each blow molded container in the sample. This average material distribution outcome can then be compared to a standard material distribution representing a nominal blow molded container to obtain an average material distribution variance to provide a signal based on the comparison back to the manufacturing process.

The inspection process must be automated to provide the desired continuous feedback to the manufacturing process. The inspection process is most desirably accomplished by transmitting light through the molded article in the vicinity of the expected location for each material distribution indicator. A plurality of sensors is provided that are capable of sensing light transmitted through the article, with each sensor capable of changing states upon receiving such transmitted light showing the location of the material distribution indicators. A lens or lens system can be employed to capture portions of the transmitted light which is then focused on a sensor such as a line linear array reader or charged coupled device camera. An output from the array reader or CCD camera can then be employed to develop a feedback signal for use by the manufacturing control system to control one or more steps of the manufacturing process.

The present invention thus provides for the production of stretch blow molded articles with non-destructively and directly controlled dimensions, such as material thickness distribution throughout the profile of stretch blow molded articles, and for consistent quality control across platforms and production facilities, ensuring that an optimum article is consistently produced with desirable performance characteristics such as burst strength, deformation, and stress cracking.

The method of the present invention for producing a stretch blow molded article having at least one dimension within a preselected range includes the step of injection molding the parison so that a parison exterior surface includes at least one indicator, typically a protruding circumferential ring or ridge, each indicator disposed at a preselected position on the parison exterior surface and formed by contact with a differentially dimensioned portion, typically a groove or indention, disposed at a preselected location on a generally smooth injection mold cavity interior surface. Where the method is carried out with a series of blow molds, the method of the present invention can include the step of blow molding an article from the parison so that an exterior surface of one article of the series includes at least one mark to identify and/or distinguish the output of one of the series of blow molds from the output of the remaining molds of the series so that articles from the same mold or station can be compared to each other and/or to an established standard.

The method of the present invention also includes inspecting the molded articles to determine whether the at least one indicator is positioned within a tolerance zone. The inspecting step is performed by situating at least one source of light and at least one positionally discriminating optical receiver, such as a CCD camera, adjacent to the output of the series of molds so that the light from the source projects through the molded container or other article and on to the optical receiver. Each optical receiver determines the position of an indicator on each passing blow molded article and provides an output signal indicative of the indicator position. The output signals from the optical receivers are then processed to compute the corresponding material distribution of each molded article from which the data was derived. The computed material distribution information can then be employed to control a subsequent step of the manufacturing process, such as an individual molded article rejection or ejection step, and/or a prior step of the manufacturing process, such as radiant heating control to modify the thermal profile of the parisons prior to the blow molding process.

It is an object of the present invention to provide an apparatus for producing a blow molded article having at least one consistent and controlled dimension. This object is achieved by providing an apparatus for producing a blow molded articles utilizing direct, non-destructive analysis of the stretch blow molded article to control at least one manufacturing variable. This control of at least a portion of the manufacturing process through a substantially continuous analysis of one or more indicators molded on the surface of the molded article has the advantage of permitting a closer and more responsive control of the manufacturing process through non-human intervention means, which allows for greater reliability than previously possible.

Further objects, features and advantages of the present invention will be apparent from a study of the following portion of the specification, and the attached drawings setting forth a preferred embodiment of the present invention illustrating the best mode of carrying out the invention presently perceived in a commercial environment, although it should be understood that various modifications can be accomplished within the parameters of the present invention.

DESCRIPTION OF THE PREFERRED EMBODIMENT

Figure 1:
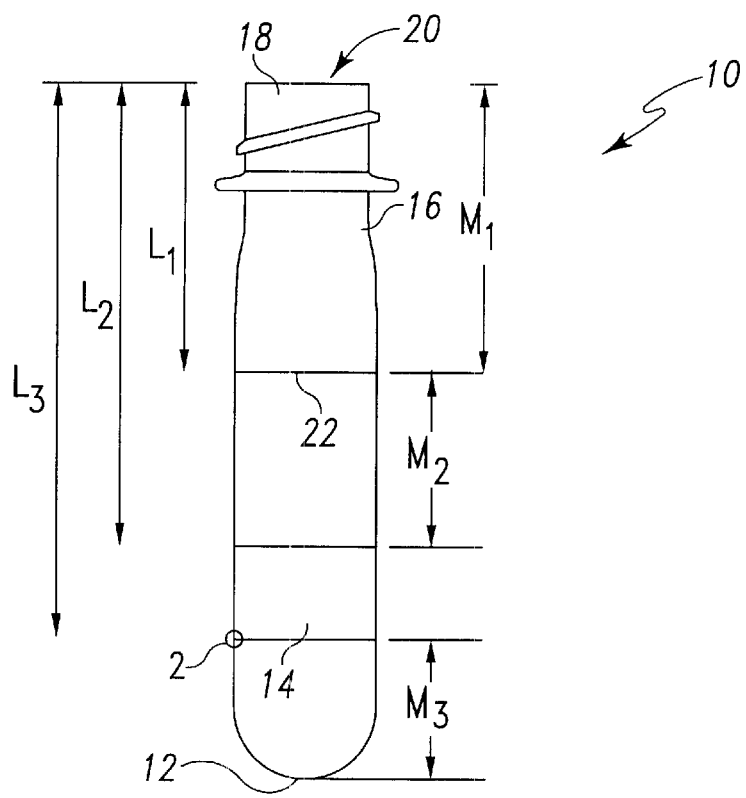
FIG. 1 is a side elevation view of a parison adapted for use in the present invention that includes three indicator rings.
Figure 2:
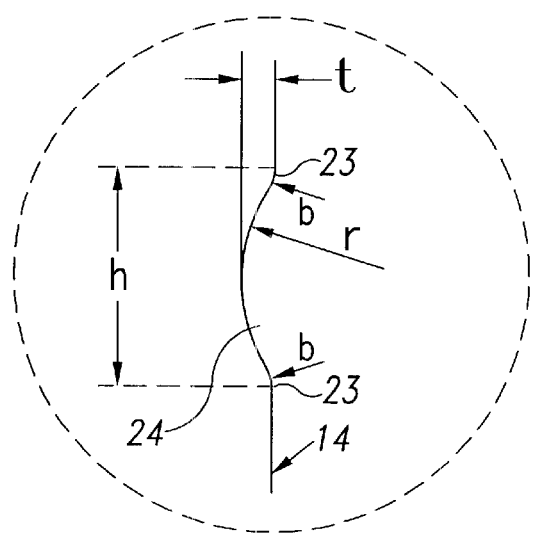
FIG. 2 is an enlarged detail sectional view of portion 2 of the side wall of the parison shown in FIG. 1 illustrating the configuration of one of the indicator rings.

A parison 10 according to the present invention is generally formed by an injection molding process to include a closed end 12, a side wall portion 14, a neck portion 16, a finish portion 18 and an open end 20 as shown in FIG. 1. The parison 10 also includes at least one, and typically two or more, material distribution indicators 22 generally formed as a protruding circumferential ring or ridge 24, one of which is shown in detail in FIG. 2. It will be appreciated by those skilled in the art that the protruding circumferential rings or ridges 24 are formed during the injection molding process by corresponding grooves on an interior surface of the injection mold cavity, not shown, generally formed by a precision grinding process. If the parison is formed of PET or other similar resin, the rings or ridges 24, also known as distribution indicators, will usually have a horizontal dimension t of between about $2.5 \times 10^{-4}$ cm and $12.5 \times 10^{-2}$ cm, and a vertical dimension h of between about $2.5 \times 10^{-4}$ cm and $2.5 \times 10^{-1}$ cm. The horizontal dimension t must be small enough to permit, after cooling, extraction of the parison from a non-split mold. The vertical dimension h must be sufficient to cause an optical disturbance of light passing through the molded article so that the location of the ring can be detected. An exemplary ring 24, as shown in FIG. 2, is defined by a ridge having a radius r of about 0.3 mm, a vertical dimension h of about 0.4 mm and a horizontal dimension t of about 0.05 mm. The upper and lower edges 23 of the ring 24 are formed by blending radii b which in the exemplary ring are about 0.075 mm. The number and positioning of the rings 24 is, of course, subject to variations in design that can depend upon, for example, the size and type of article to be formed from the parison.

Figure 3:
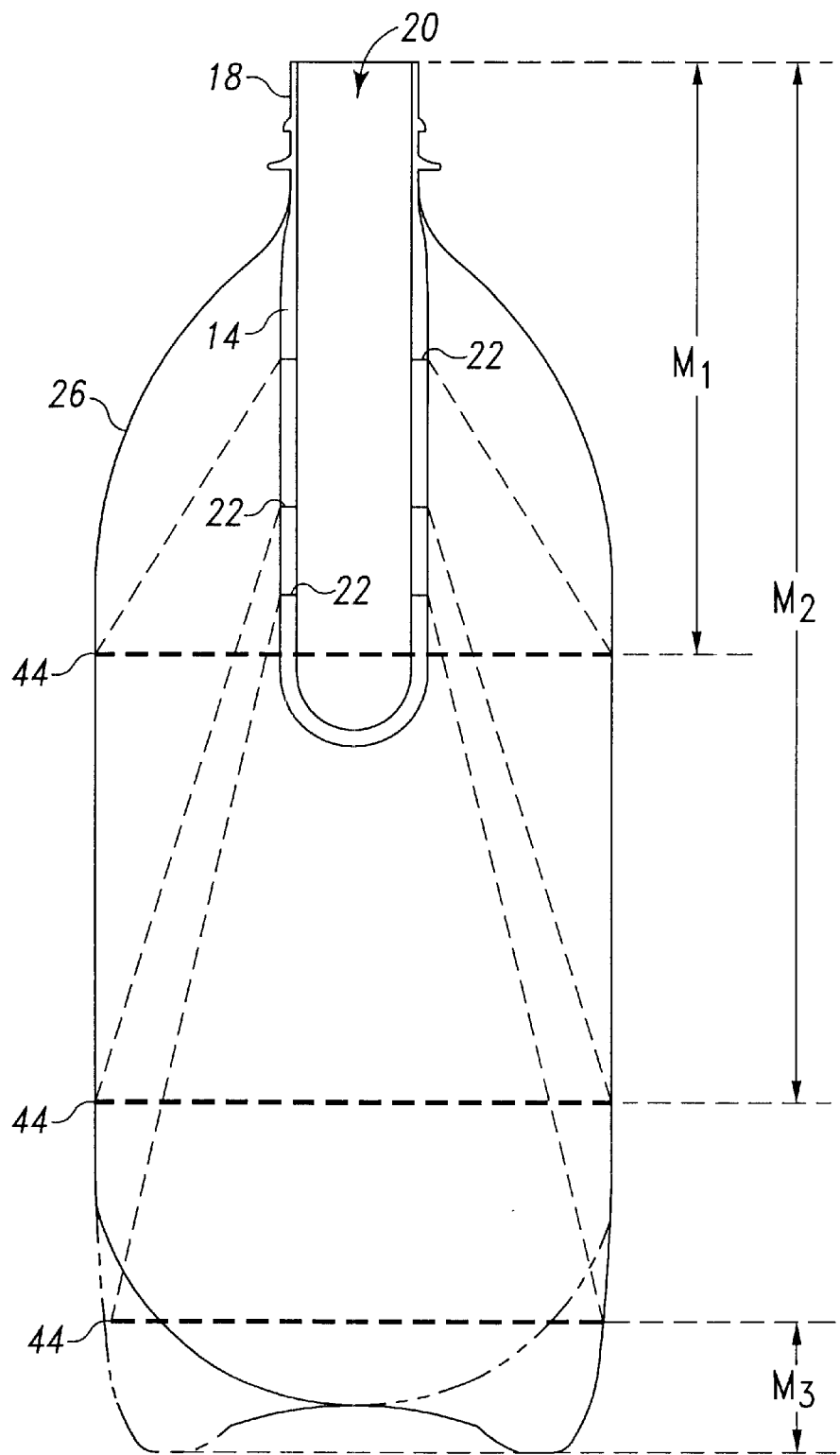
FIG. 3 is a schematic view of the expected translation of the indicator rings on the parison to various portions of the blow molded article as a result of the stretch blow molding process.
Figure 4:
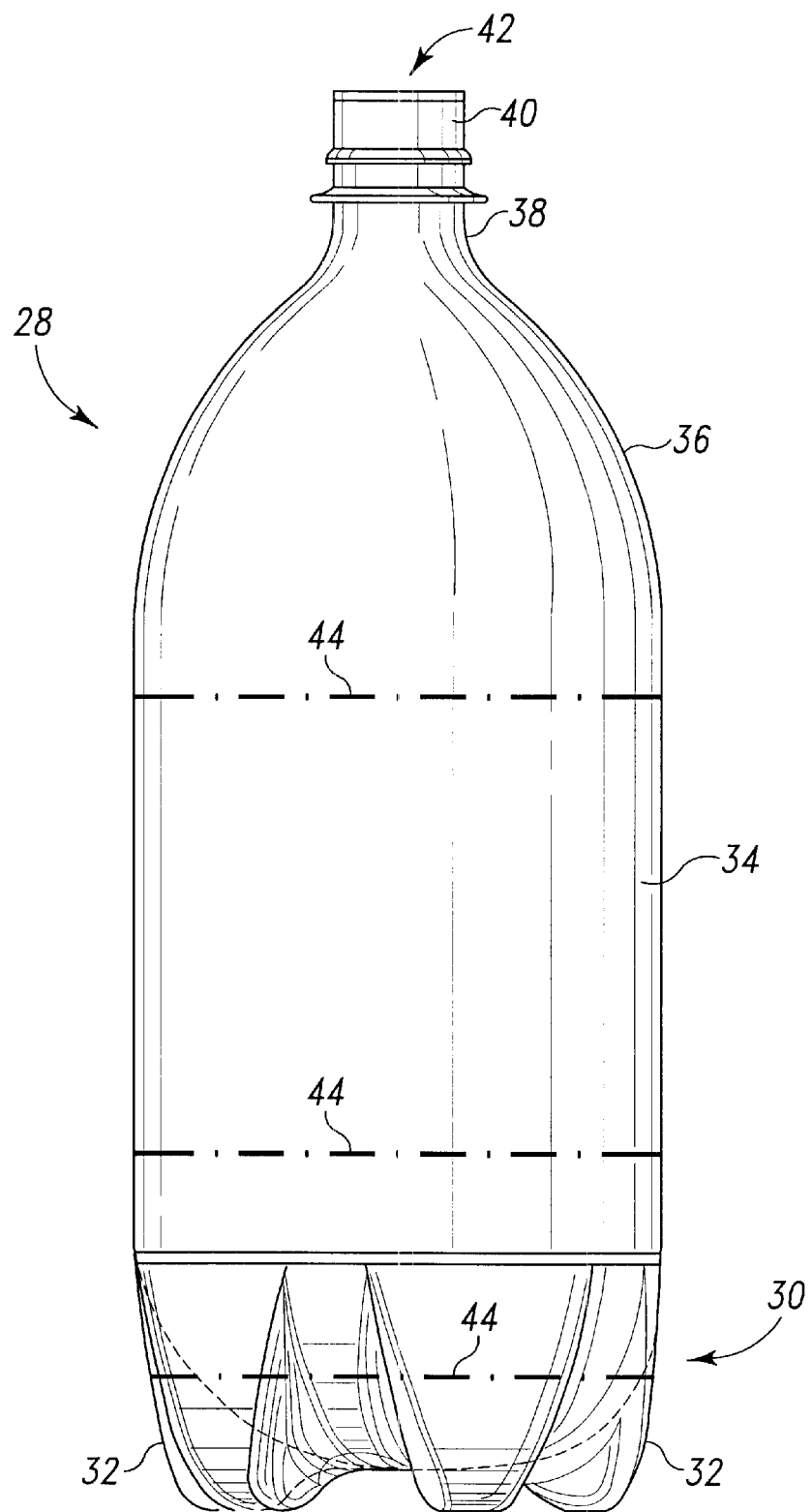
FIG. 4 is a side elevation view of a blow molded container made from the parison of FIG. 1 reflecting expected translation of the indicator rings to the container side wall and footed portions.

The rings 24 on the parison 10 are translated to corresponding positions on the blow molded article 26 as shown in FIG. 3. A typical article 26 molded using this invention is a PET container 28 suitable for use in bottling carbonated beverages as illustrated in FIG. 4. The container includes a bottom portion 30 which is illustrated to include a plurality of feet 32 permitting the container to be self-standing, without the aid of any separate base cup, however this base structure is subject to considerable variation in design well known in the art. A side wall portion 34 extends upward from the base portion 30 and is generally biaxially oriented during the blow molding process. A shoulder portion 36 extends upward from the side wall portion 34 to a neck portion 38. A finish portion 40, generally identical to the finish portion 18 of the parison 10, including an open end 42 completes the general structure of the container 28. The container 28 is shown to have a plurality of material distribution indicators 44 that correspond to the translation of the rings 24 on the parison 10 to the container 28 as a result of a stretching and circumferential expansion of the parison 10. The distribution indicators 44 appear on the blow molded container as slight transparent distortion lines extending around the circumference of the container 28 generally as shown in FIG. 4, which are the consequence of the material distribution indicators 22 present on the parison 10 and not the product of any groove or ridge present in the blow mold in which the container 28 is blow molded.

As a general rule, one initially locates the material distribution indicator rings 44 by forming a container 28 without any such rings from its related parison 10, which also has no such rings. The container 28 is then cut into sections along the vertical extent of the container at selected locations corresponding to the desired position for the indicator rings 44. The material distribution, that is the mass, of each section is determined by weighing the sections on a scale. The weight of each section is then recorded, e.g., M1, M2, and M3. This data is then mapped back to the parison 10 to determine where this material is located in the parison 10 before it is blow molded into the container 28. The mass distribution in the parison 10 can be computed very accurately due to its uniform density and its volume calculated from the known dimensions of the core and cavity defining the molding space in which the parison is injection molded. Due to conservation of volume and mass during the molding process, the section below, between, and/or above the distribution indicators on the parison must weigh exactly the same as the sections of the container below, between and/or above the distribution indicators. The lines 22 are then fixed in relation to an end of the parison, e.g., the finish end, by precision grinding corresponding grooves on an interior surface of the injection mold cavity in which the parison 10 is to be formed at computed distances, e.g., L1, L2, and L3. With some experience, it may also be possible to correctly position the rings 24 on the parison 10 merely after a theoretical or mathematical evaluation of the parison and the container sought to be formed from the particular parison. The desired parison mold configuration is then reproduced or copied into any number of similar molds suitable for commercial production of identical parisons 10 including the mapping rings 24 for the particular container design.

Figure 5:
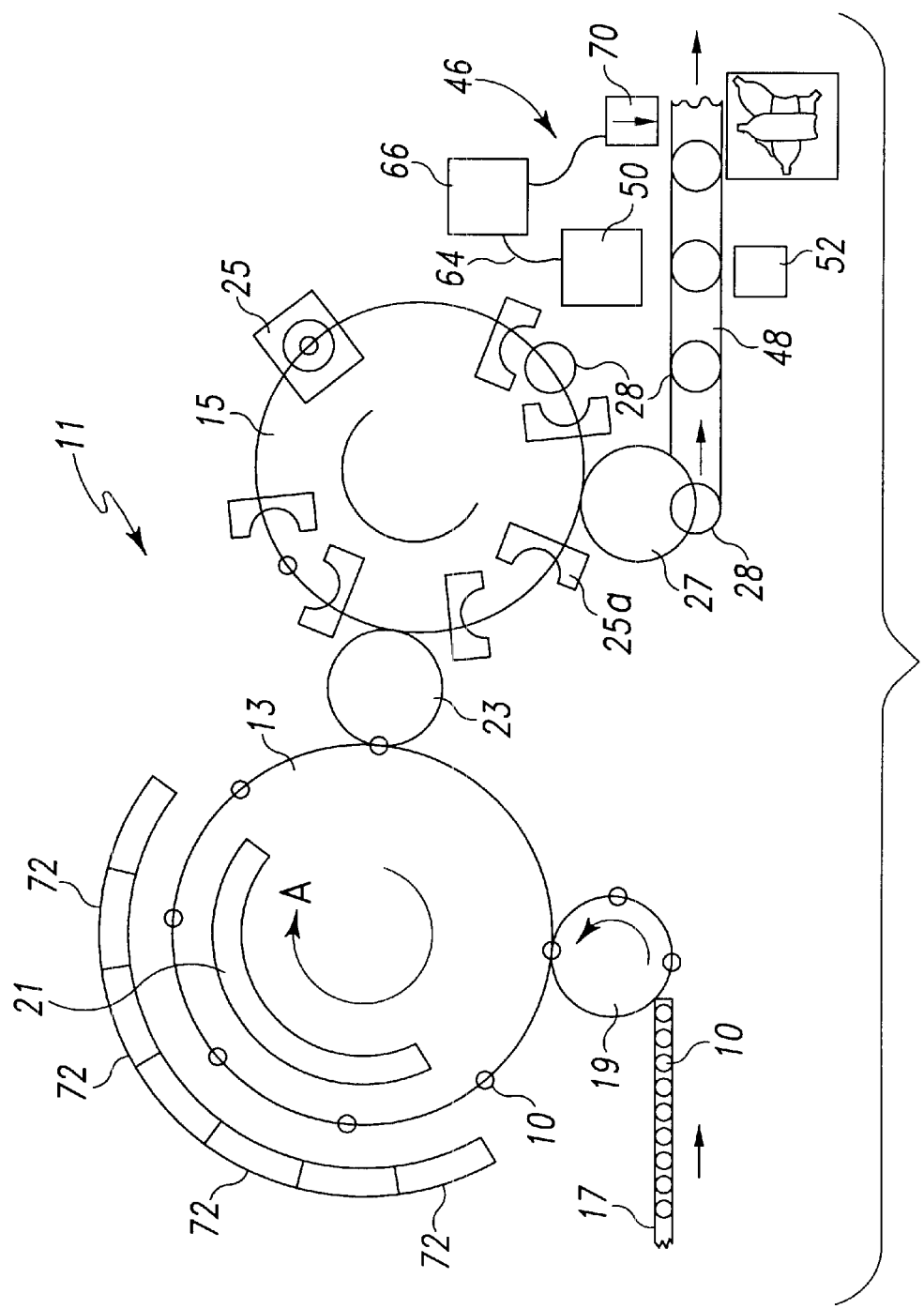
FIG. 5 is a plan schematic presentation of a parison re-heating and blow molding operation employing the present invention.

The parisons 10 can then be used in the commercial production of the particular container design in a re-heat and blow molding process employing any number of blow molds from a single cavity machine to a high speed multiple cavity machine such as a SideI SBO-24 or a Krupp-Corpoplast Blowmax-16. A serial multiple cavity machine 11 is schematically illustrated in FIG. 5 to include a re-heat section 13 followed by a blow molding section 15. A feeder 17 feeds a linear progression of parisons 10 into a first transfer mechanism 19. The transfer mechanism 19 loads the parisons 10 into the re-heat section 13 which is driven at a constant speed in the direction of arrow A. As the parisons 10 travel through the reheat section 13, they are exposed to a plurality of radiant heater sections 72. Each of the radiant heater sections 72 contains a plurality of horizontally disposed heater elements 74 fixed in spaced proximity from the line of parisons 10 as shown schematically in FIG. 6. The radiant heaters 74 can be located on only one side or on both sides of the line of parisons 10. Where the radiant heaters 74 are located on only one side of the line of parisons 10, a reflector 21 may be positioned opposite the plurality of heater elements 74 to reflect the radiant energy initially passing the parisons 10 back toward the parisons.

The heater elements 74 are conventional, being made in accordance with U.S. Pat. No. 3,436,524 and improvements thereon. The amount of heat delivered by each of the heater elements 74 to the passing parisons can be controlled, either by adjusting the spacing of the element from the line of parisons as suggested by U.S. Pat. No. 5,688,466, or by adjusting the electrical power applied to the element as suggested by U.S. Pat. No. 4,079,104 and others. As the parisons 10 travel through the reheat section 13, they are rotated about their longitudinal axis Y so they are circumferentially uniformly heated. Once each parison 10 is reheated appropriately by the reheat section 13, the parisons is transferred by transfer mechanism 23 into one of the blow molds 25 in the blow molding section 15 where it is blow molded into an article such as container 28 as described previously. The blow molded articles 26 are then transferred by transfer mechanism 27 onto conveyor 48. It will be appreciated by those skilled in the art that. alternative schemes for producing blow molded articles are well known including those employed by so called single step machines, such as an AOKI 500 series, that first injection mold a set of parisons, and then blow mold the set of parisons into a set of the desired articles in a continuous process utilizing, at least in part, the heat from the injection molding process to facilitate the blow molding process.

Figure 7:
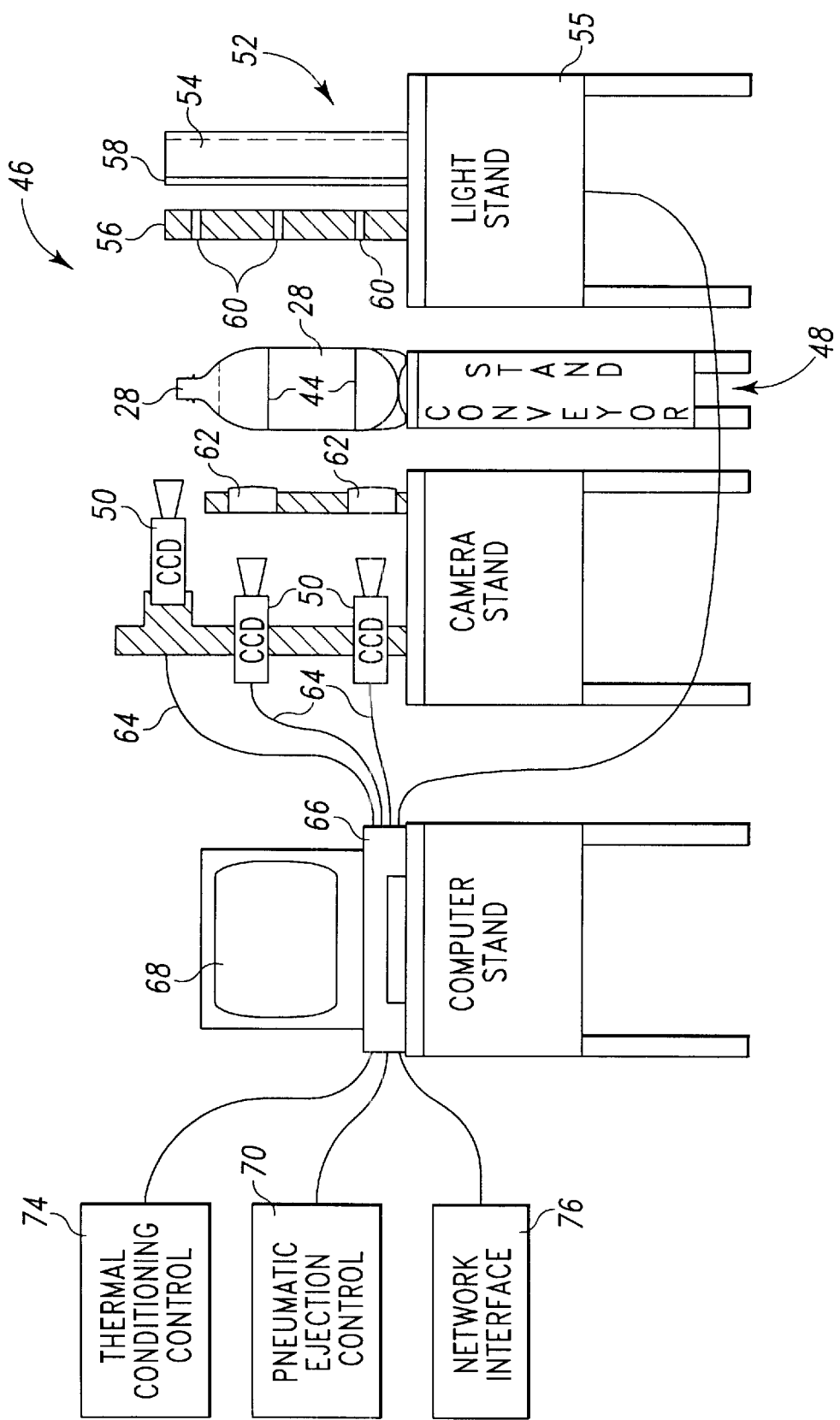
FIG. 7 is a schematic presentation of an inspection apparatus situated adjacent to a conveyor transporting a series of blow molded containers made in accordance with the present invention.

Each of the containers 28 streaming out of any blow molding process using the present invention will have the material distribution indicator rings 44, which can be detected by an appropriate detecting system 46, an example of which is shown in FIG. 7. The detecting system 46 can be located either inside or outside of the blow-molding machine, and can employ either a direct lighting system or a back lighting system to illuminate the indicator rings 44. A preferred detecting system 46 employing back lighting straddles the conveyor 48 preferably within about 6 meters of the blow molding machine as shown in FIGS. 5 and 7. The detecting system 46 includes a plurality of light detectors, such as array readers or CCD cameras 50, positioned at a known height on one side of the conveyor 48 and a back lighting system 52 located directly on the opposite side of the conveyor 48. A preferred camera is a DVT-600 available from DVT Corporation, Norcross, Ga. The lighting system 52 comprises a light source 54 which is preferably a fiber optic line light, such a Fostic 12 light model AO8912. The light source 54 is coupled to a strobe unit in light stand 55 to produce a momentary bright vertical line of light when each container 28 passes from which data is desired. The light system 52 also includes a slit panel 56 and a diffuser 58. The slit panel 56 is generally opaque except for slits 60 at certain selected vertical locations in general alignment with the expected location of the top 20 of the container 28, and with the expected location of one or more of the indicator rings 44 located on the side wall of the container 28. The vertical height of each slit 60 is related to the distance from the slit 60 to the lens 62 and the maximum expected deviation in the location of the corresponding marking on the container. In the preferred embodiment, the slits 60 have a vertical height of between about 1.5 and 6.5 mm, preferably about 3.175 mm and a horizontal width sufficient to illuminate at least a central portion of the container, preferably about 15 mm. The diffuser 58 functions to make the light essentially uniform over the entire area of each of the slits 60.

One of the CCD cameras 50 is preferably aligned with the expected location of the top of the passing containers 28, and is used to detect containers which, for one reason or another, do not match the height criterion for such containers. One or more additional CCD cameras 50 are positioned directly opposite a slit 60 so that light from the slit passing through a container 28 is directed toward one of the cameras 50. The detecting system 46 preferably also includes an achromatic lens 62 situated between the containers on the conveyor and each camera 50 aligned with the indicator rings 44. In the preferred embodiment the lenses 62 have a focal length of between about 50 mm and 200 mm and are designed to collimate the light that has passed through the container toward the camera 50, rather than focus an image of the container side wall 34. Light from the back lighting slit 60 generally passes straight through the container 28, except where a material distribution indicator ring 44 is located. The indicator ring 44 deflects the light from its straight line path so that a variation of light intensity in the general shape of a horizontal line occurs. It will be appreciated that any indicator ring 44 located outside the side wall portion 34 of the container 28 represents a special situation that may not be as suitable for processing. The typically horizontal line of intensity variation directed toward the camera 50 by the lens 62 will occur at different locations depending upon variations in the location of a given indicator ring 44. The camera 50 includes an output that can be fed through line 64 to a computer 66 that includes a visual display screen 68 and on which certain functional software has been previously loaded to handle the information output from the cameras 50.

Broadly, the detecting system 46 locates each of the indicator rings 44 and the top of the container 28 based on the known vertical position of the conveyor 48 relative to the various cameras 50. As the containers 28 travel down the conveyor 48 from the blow molding machine, they pass through the detecting system 46. Each container triggers a photo eye, micro-switch, or other sensor, just prior to the CCD cameras 50, which triggers the cameras 50 and the strobed light 54. The cameras 50 detect the physical position of the indicator rings in relation to the bottom of the container 28 as defined by the supporting surface of the conveyor 48. The height of the container 28 is also detected. This information is then sent to the computer 66 for evaluation by appropriate software previously loaded on the computer 66. The software preferably converts this data into container sectional weights in relationship to the areas of the inspected container. This information can be compared to the permissible weight specifications for those sections.

The computer preferably automatically alerts the operator of containers that are out of specification by using graphical alarms, sirens, and/or beacons, and can be employed to eject sufficiently nonconforming containers from the passing stream using, for example, a pneumatic ejection control mechanism 70. The section weight information is also preferably used for statistical analysis and for automatic ejection of failed containers, that is containers that are outside certain preset margins. The system can also be network capable by means of an Ethernet or other network interface 76. Information can be stored and sent via a manufacturing plant's network where the information can be monitored and recorded in the plants SPC system.

Figure 8A:
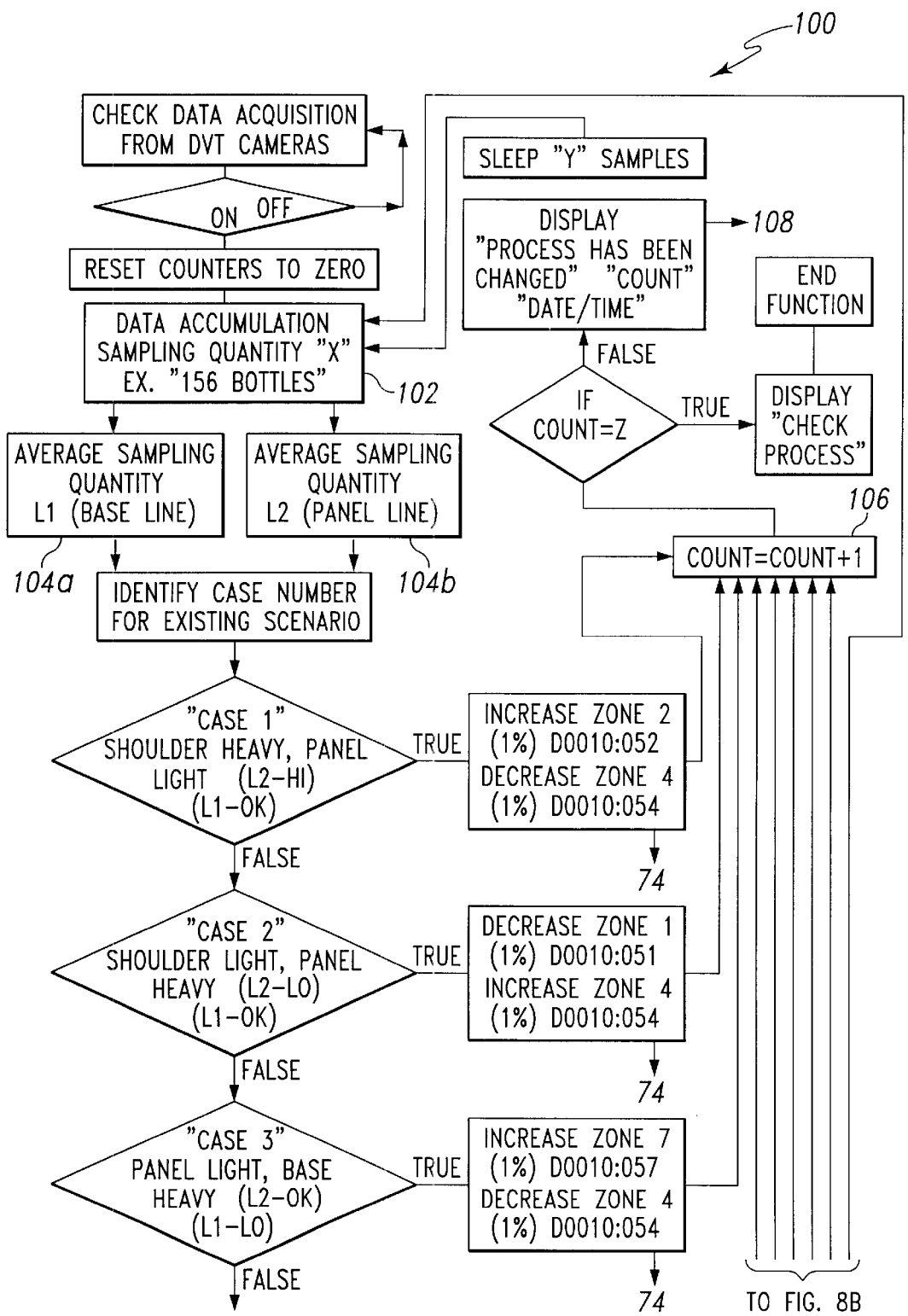
FIGS. 8a and 8b are a flow diagram of the blow molded article evaluation process carried out by the inspection apparatus shown in FIG. 7.
Figure 8B:
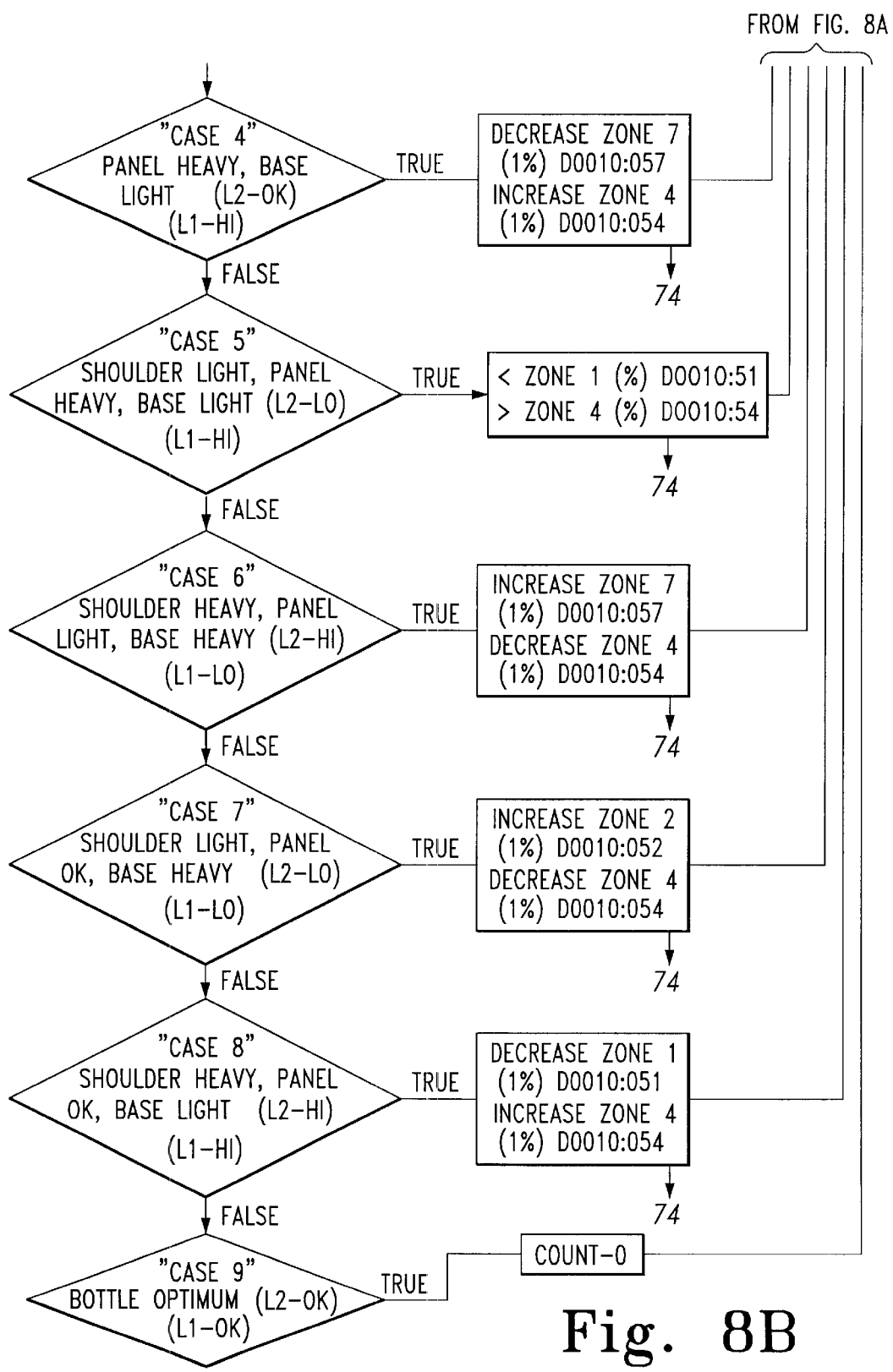

The data collected can also be used for feedback control so that the information processed by the computer 66 based on the monitoring of bottle conformation affects the processes of the blow molder making any necessary process changes to the machine in order to keep the bottle within the preset specifications. The specific code for accomplishing these tasks is subject to substantial variation. The flow chart shown in FIGS. 8*a* and 8*b* illustrate the various criteria applied by an exemplary system employed to modify the re-heating of the parisons 10 based upon the average of a sample quantity of containers. The flow diagram 100 in FIGS. 8*a* and 8*b* is illustrative of a program to be used with radiant heater sections 72 employing seven heater elements 74 numbered sequentially 1–7 from the bottom to the top as shown in FIG. 7.

The electrical power to each heater element 74, which is generally less than 100% of the possible power that can be applied, can be easily adjusted by an electrical circuit controlled by a thermal conditioning control 72 coupled to an output of computer 66. It will be appreciated by those skilled in the art that the change made by control 74 need not necessarily be to only a single heater element, but can be to any desired groups of heater elements. It will also be appreciated that when the heating profile is appropriately adjusted, the heat delivered to the passing parisons 10 will be such that the position of the indicator rings 44 will be positioned as desired on the surface of the containers 28. By contrast, when the heating profile is not appropriate, one or more regions of the passing parisons 10 will arrive at the blow molding section 15 either too cool or too hot, in which case the polymer forming the parison will experience insufficient or excess stretching during the blow molding process, thus displacing one or more of the indicator rings 44 from their prescribed position, which will be observed by the detection system 46.

Figure 6:
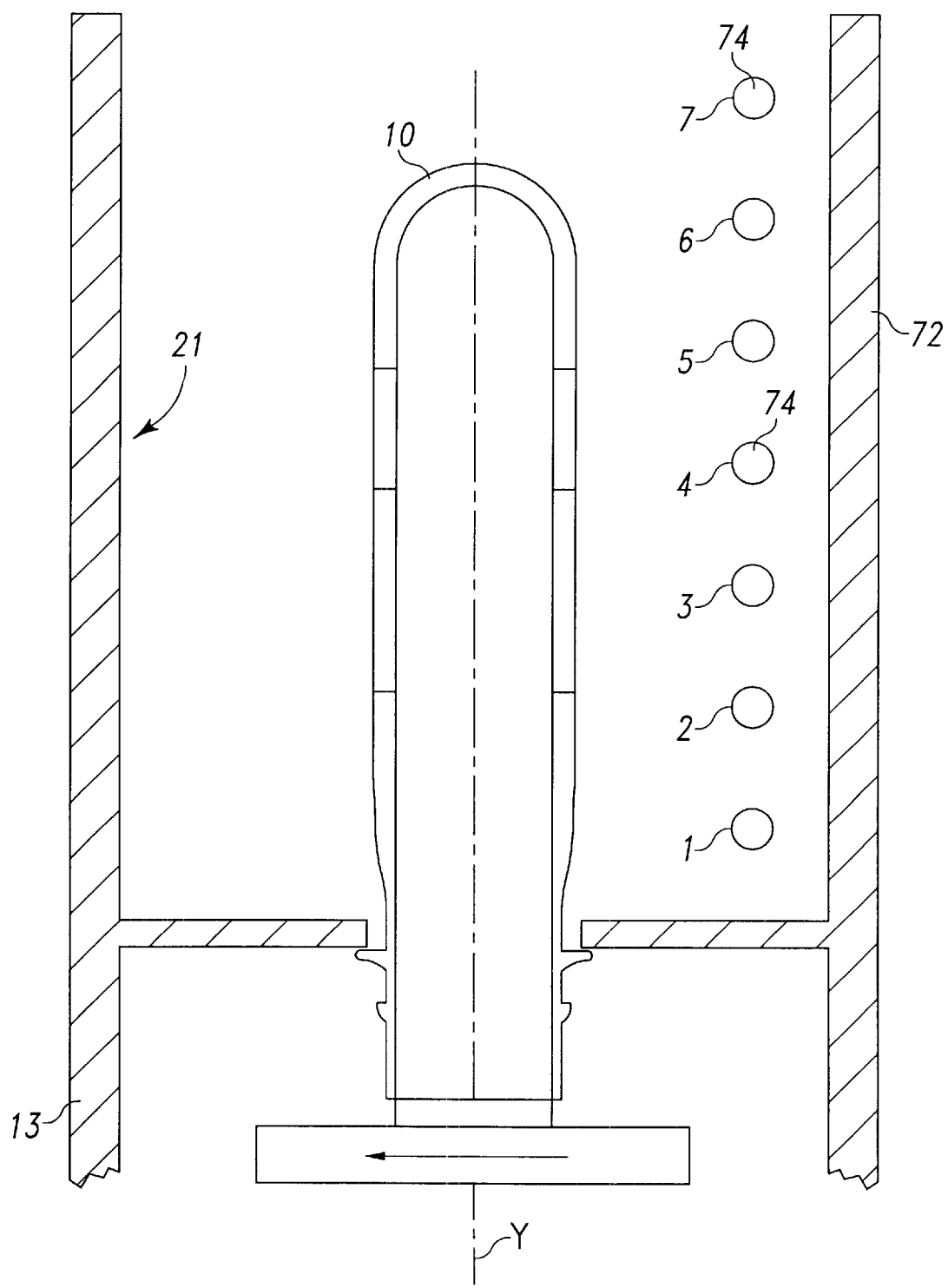
FIG. 6 is a schematic illustration of a parison heater used in a re-heating process controlled by the present invention.

The data is collected from a blow molding system 11 illustrated schematically in FIGS. 5 and 6, showing a system employing a plurality of radiant heater sections 72 to reheat a line of parisons 10 in accordance with the present invention as they are conveyed by the radiant heater sections 72. The program implemented by the computer 66 is generally intended to take readings of a series of X containers, where X is a number selected sufficiently large to largely eliminate any statistical noise that might be present were too small a sample number selected, and as a general rule is some multiple of the number of spindles in the reheating oven employed in the process, e.g., X=156 for a SideI SBO-10. The readings of the positions of the indicator rings 44 are accumulated by accumulator 102, and averaged to arrive at an expression for the average position of each observed indicator ring 44 over the sample quantity X. In this example, the number of indicator rings 44 employed in the analysis is only two, which divides the container 28 into three vertical areas; namely, the shoulder 36, the panel 34, and the base 30. The neck 38 and finish 40 is substantially unmodified by the re-heating and blow molding process and, accordingly, need not be considered in this analysis of the finished containers 28.

The averaged value 104*a* and 104*b* is then identified with an identifying case number based on the observed variation in mass from the prescribed criteria for the container 28. The identifying case number is determined by serially considered in a logic ladder identified as Case 1 through Case 9, to determine what action, if any, should be taken to correct the heating profile to which the parisons 10 are subjected. The program 100 prescribes a fixed incremental change, e.g., 1%, to the power applied to one or more of the heating elements 74 by selecting the applicable Case number, other than Case 9 (Bottle Optimum) in which Case no change is made. If any Case is identified other than Case 9, the program also increments a "Count" number in store 106. The Count number can be stored with the heater settings, date and time of change, and other desirable information in a data storage area 108 for subsequent analysis. A change in the Count number can also trigger a display indicating the incrementation.

Following an incrementation, the sampling process preferably goes into a "sleep" mode for a time that is sufficiently large that any impact on the blow molds by any change in parison heating has stabilized. After some time, usually measured by the passing of a sufficient number of containers Y, the data accumulation process resumes at accumulator 102. The control scheme diagrammed in FIGS. 8a and 8b uses the line positions read by the CCD cameras 50 and compares those line positions to control modification case options. In the example presented by FIGS. 8a and 8b, there are 3n options where n=the number of mapping lines on the container. For the case of the example with two lines on the container, there are nine optional control cases. The control system of the present invention continuously records the line positions for a specified number of parisons depending on the blow-molding machine. If the average position of any of the lines deviates beyond a specified tolerance, the control system selects the appropriate control case for that condition. The control case makes a modification to the oven lamps heat percentage profiles, or some other parison preparation characteristic, through direct communication with the blow-molder's programmable logic controller or control computer. The system also records the effects of this change on the line positions. If the lines are not within their specified locations the control system implements another correction. This continues until the lines are within specification. If the system cannot make the necessary corrections to the line positions after a specified number of attempts, the change in the Count number matches a preset number Z, and alternative instructions may be sent to the display, or perhaps an alarm condition may be sounded and or signaled indicating that the process requires human inspection and possible intervention, including possible re-setting of the processing and data accumulation criteria.

As indicated previously, the system can be employed with blow molding machines that process the heated parisons in either a serial or batch process. In a serial process, such as that employed by an SBO-24, a series of blow mold cavities are employed, each of which may have slightly different thermal and other characteristics. Additionally, the containers made in such an apparatus exit from the blow molding apparatus in serial order, as shown schematically in FIG. 5, reflecting the order of the individual blow molding cavities or mold stations used in the apparatus. In such systems, the detecting system 46 of the present invention can be used to record data in direct relationship with the mold station on which each bottle was produced.

This is accomplished by scribing a selected one of the series of blow mold cavities, 25a, with an indicating mark such as a circumferential groove near the edge of the field of view of one of the CCD cameras 50. When the system 46 detects this unique mark, the software can be modified to recognize this container as coming out of a "last" or "first" blow molding station 25a in the series 25a, 25b, 25c, . . . 25n, and to begin the next inspection with specific correlation to the blow mold station. The modified software contains a counting algorithm, which identifies each consecutive container 28 with its corresponding blow mold 25. The accumulator 102 can then segregate the information relating to each blow molding station 25 in the series to detect variations in average performance or any specific blow mold 25i that might indicate a problem not having its origin in the parison re-heating process.

While some significant changes might be necessary to the illustrated preferred embodiment, and to the software previously described, the present invention can also be employed in a so-called one step machine to control the temperature conditioning of the parisons between the injection stage and the blow molding stage of such a machine. The present invention having been described in its preferred embodiments, it is clear that the present invention is susceptible to other numerous modifications and embodiments within the ability of those skilled in the art and with or without the exercise of the inventive faculty. Accordingly, the scope of the present invention is defined as set forth by the scope of the following claims.

What is claimed is:

1. A method for inspecting the material distribution of a sequence of blow molded containers in a continuous production process, the method comprising:

providing injection molded axially extending parisons, each parison having at least one indicator of material distribution at a predetermined position along the axial extent of the parison;

thermally conditioning the parisons in the continuous production process to a temperature profile suitable for blow molding;

blow molding the heated parisons so that each material distribution indicator is transformed to a corresponding axial location along the blow molded container;

detecting, from at least some of the blow molded containers in the production process, the axial location of the indicator relative to a control location;

determining for the at least some blow molded containers a material distribution outcome based on the detected axial locations of each indicator accumulating data representative of the material distribution outcome for a group of containers;

computing an average material distribution characteristic for the group of containers;

classifying the average material distribution characteristic for the group of containers in one of a pre-defined set of classes; and providing a signal based on the classification.

2. The method of claim 1 further comprising the step of: forming each material distribution indicator on each parison having a horizontal dimension t of between about $2.5 \times 10^{-4}$ cm and $12.5 \times 10^{-2}$ cm, and a vertical dimension h of between about $2.5 \times 10^{-4}$ cm and $2.5 \times 10^{-1}$ cm.

3. The method of claim 1 wherein the detecting step is performed by an optical detector device detecting a variation in light intensity caused by a transformed indicator on an exterior surface of the blow molded container in the form of a circumferential ridge.

4. The method of claim 1 further comprising the steps of:

comparing the determined material distribution outcome for each container to a previously defined tolerance range, and generating a signal causing a blow molded container to be removed from the production process if the determined material distribution outcome for the containers is outside a tolerance range.

5. The method of claim 1 wherein the containers are blow molded in a plurality of blow molding stations according to a continuously repeated cycle, the method further comprising:

providing a scribe in a selected blow molding station;

molding a mark on each respective container blow molded in the selected blow molding station;

detecting the mark to identify the marked container and each subsequent unmarked container in the continuous cycle;

grouping the determined material distribution outcome data for the marked and each of the subsequent unmarked containers to correlate to each of the blow molding stations; and reviewing the grouped data to detect any problem related to one of the blow molding stations.

6. A method for inspecting the material distribution of a sequence of blow molded containers in a continuous production process, the method comprising:

providing injection molded axially extending parisons, each parison having at least one indicator of material distribution at a predetermined position along the axial extent of the parison;

thermally conditioning the parisons in the continuous production process to a temperature profile suitable for blow molding;

blow molding the heated parisons so that each material distribution indicator is transformed to a corresponding axial location along the blow molded container;

detecting, from at least some of the blow molded containers in the production process, the axial location of the indicator relative to a control location;

determining for the at least some blow molded containers a material distribution outcome based on the detected axial locations of each indicator;

selecting a sample of containers from the sequence of stretch blow molded containers;

calculating an average material distribution outcome for the sample based on the determined material distribution outcome for each blow molded container in the sample;

comparing the average material distribution outcome to a standard material distribution representing a nominal blow molded container to obtain an average material distribution variance; and providing a signal based on the comparison.

7. The method of claim 6 further comprising the step of adjusting the thermal conditioning of the parisons from the signal based on the comparison.

8. The method of claim 7 wherein the sample is a moving sample and the average is a rolling average.

9. The method of claim 6, wherein the detecting step further comprises producing a light signal on one axial side of the container which travels through the container and through a lens to an imaging device on the opposite axial side of the container.

10. A method for controlling the material distribution of a sequence of stretch blow molded containers in a continuous production process, the method comprising:

providing injection molded axially extending parisons, each parison having at least one indicator of material distribution at a predetermined position along the axial extent of each parison;

heating the parisons in the continuous production sequence by exposure to a plurality of separate heating zones disposed along the axial extent of the parisons;

stretch blow molding the heated parisons so that the material distribution indicator is transformed to a corresponding position along the axial extent of the blow molded container;

detecting for each blow molded container an axial location relative to a control location for each indicator of material distribution for each blow molded container;

determining for each blow molded container a respective material distribution outcome based on the detected axial location of each indicator;

selecting a sample from the sequence of stretch blow molded containers;

calculating an average material distribution outcome for the sample based on the determined material distribution outcome for each blow molded container in the sample;

comparing the average material distribution outcome to a standard material distribution outcome for a nominal container to obtain an average material distribution variance;

comparing the average material distribution variance to a set of predetermined variance case options;

selecting one variance case option based on the comparison; and implementing a process adjustment related to the selected variance case option.

11. The method of claim 10 further comprising the step of:

adjusting in each separate heating zone the heat applied to subsequent parisons according to the selected adjustment.

12. The method of claim 11 further comprising the step of:

correlating historical adjustments made to correct variations in material distribution of actual blow molded containers to a variance case option to select one of a set of possible process adjustments.

13. The method of claim 11 further comprising the step of:

forming the parison indicator at a horizontal dimension t of between about $2.5 \times 10^{-4}$ cm and $12.5 \times 10^{-2}$ cm, and a vertical dimension h of between about $2.5 \times 10^{-4}$ cm and $2.5 \times 10^{-1}$ cm.

14. A control system for controlling the material distribution for a sequence of stretch blow molded containers in a continuous production process, the system comprising:

a parison supply section supplying a plurality of injection molded, axially extending parisons, each parison having at least one indicator of material distribution at a predetermined position along the axial extent of the parison;

a parison thermal conditioning section having a plurality of separate axially differentiated conditioning zones to vary the temperature along the axial extent of the parisons;

a blow molding section transforming the thermally conditioned parisons into axially extended, blow molded containers having at least one indicator of material distribution at corresponding positions;

an optical detector sensing the axial location of at least one indicator of material distribution on each blow molded container;

a computer having an input coupled to the optical detector, the computer determining a material distribution outcome for each blow molded container, accumulating data representative of the material distribution outcome for a group of containers, computing an average material distribution characteristic for the group of containers, classifying the average material distribution characteristic in one of a pre-defined set of classes, and providing a signal to an output of the computer based on the selected classification; and a control feedback circuit coupled to the output of the computer and to one of the parison supply section, the parison thermal conditioning section and the blow molding section implementing at least one predetermined process adjustment designed to modify the material distribution of subsequent blow molded containers.

15. The control system of claim 14 wherein the blow molded container is a bottle and wherein the transformed indicator is a circumferential ridge on an exterior surface of the bottle and the ridge being detectable by the optical detector.

16. The control system of claim 15 wherein the ridge is positioned on at least one of the shoulder, the panel, and the base of the bottle.

17. The control system of claim 14, wherein the parison indicator has a horizontal dimension of between about $2.5 \times 10^{-4}$ cm and $12.5 \times 10^{-2}$ cm, and a vertical dimension of between about $2.5 \times 10^{-4}$ cm and $2.5 \times 10^{-1}$ cm.

18. The control system of claim 14 wherein
the parison thermal conditioning section is a re-heating section including a plurality of horizontally extending and vertically spaced infrared heater elements, and wherein
the control feedback circuit is coupled to a supply of power to the heater elements to effect changes to the pattern of re-heating to which the parisons are subjected.

19. A control system for controlling the material distribution for a sequence of stretch blow molded containers in a continuous production process, the system comprising:
a parison supply section supplying a plurality of injection molded, axially extending parisons, each parison having at least one indicator of material distribution at a predetermined position along the axial extent of the parison;
a parison thermal conditioning section having a plurality of separate axially differentiated conditioning zones to vary the temperature along the axial extent of the parisons;
a blow molding section transforming the thermally conditioned parisons into axially extended, blow molded containers having at least one indicator of material distribution at corresponding positions;
an optical detector sensing the axial location of at least one indicator of material distribution on each blow molded container;
a computer having an input coupled to the optical detector, the computer determining a material distribution outcome for each blow molded container, comparing the material distribution outcomes to a plurality of preset material distribution variance characterizations, and implementing a decision sequence to select one of the preset characterizations to generate an output signal to an output of the computer; and
a control feedback circuit coupled to the output of the computer and to one of the parison supply section, the parison thermal conditioning section and the blow molding section implementing for certain of the preset material distribution variance characterizations at least one predetermined process adjustment designed to modify the material distribution of subsequent blow molded containers.

20. A method for controlling the material distribution of a sequence of stretch blow molded plastic containers in a continuous manufacturing process, the method comprising the steps of:
providing a continuous production sequence of injection molded parisons;
heating the parisons in the continuous production sequence by exposure to a plurality of axially distributed heating zones;
stretch blow molding the heated parisons into containers, the containers being output from the blow molding operation as a sequence;
identifying a characteristic of material distribution for each blow molded container in the sequence;
comparing the identified material distribution characteristic of each container to a standard material distribution characteristic for a nominal container to detect a material distribution variance;
selecting one of a predetermined set of variance case options based on the detected material distribution variance; and
implementing a process adjustment related to the selected variance case option to modify a processing variable of the manufacturing process.

21. The method of claim 20 wherein the identifying step includes the steps of
transmitting light from a selected light source through each container; and
sensing the light passing through each container from the light source at a plurality of locations to detect indicators of the material distribution of each container.

22. The method of claim 20 wherein the process adjusting step comprises modify the heating occurring in at least one of said axially distributed heating zones.

23. A method for controlling the material distribution of a sequence of stretch blow molded plastic containers in a continuous manufacturing process, the method comprising the steps of:
providing a continuous production sequence of injection molded parisons;
heating the parisons in the continuous production sequence by exposure to a plurality of axially distributed heating zones;
stretch blow molding the heated parisons into containers, the containers being output from the blow molding operation as a sequence;
selecting a sample from the sequence of stretch blow molded containers; and
calculating an average material distribution for the sample based on the detected material distribution for each blow molded container in the sample;
comparing the identified material distribution characteristic of each container to a standard material distribution characteristic for a nominal container to detect a material distribution variance;
selecting one of a predetermined set of variance case options based on the detected material distribution variance; and
implementing a process adjustment related to the selected variance case option to modify a processing variable of the manufacturing process.

24. The method of claim 23 wherein the calculating step comprises the step of
comparing an average of the identified material distribution characteristics for said selected sample to a standard material distribution for a nominal container to obtain an average material distribution variance.

25. The method of claim 23 wherein said providing step comprises the step of producing injection molded parisons with at least one indicator of material distribution at a predetermined position on each parison.

26. The method of claim 25 wherein the stretch blow molding step includes the step of transforming the at least one material distribution indicator on each parison to a corresponding position on each blow molded container.

27. The method of claim 26 where said identifying step comprises the steps of
- detecting the location of each transformed material distribution indicator on the blow molded containers relative to a control location for each indicator of material distribution; and
- identifying a material distribution characteristic of the blow molded containers based on the detected locations of the indicators.

28. A control system for controlling the material distribution for a sequence of stretch blow molded containers in a continuous production process, the system comprising:
- a parison supply section supplying a plurality of injection molded parisons;
- a parison thermal conditioning section having a plurality of axially differentiated conditioning zones to thermally condition the parisons;
- a blow molding section transforming the thermally conditioned parisons into blow molded containers;
- an optical detector sensing at least one indicator of material distribution on each blow molded container;
- a computer having an input coupled to the optical detector, the computer determining a material distribution characteristic for each blow molded container based on the input from the optical detector;
- a plurality of preset material distribution variance characterizations, and
- a decision sequence to select one of the preset characterizations to generate an output signal; and
- a control feedback circuit coupled to receive the output signal and coupled to one of: the parison supply section, the parison thermal conditioning section and the blow molding section, the control feedback circuit implementing for certain material distribution characteristics at least one predetermined process adjustment designed to modify the material distribution of subsequent blow molded containers.

29. The control system of claim 28 wherein the blow molded container is a bottle and wherein the material distribution indicator is a circumferential ridge on an exterior surface of the bottle, the ridge being detectable by the optical detector.

30. The control system of claim 29 wherein the ridge is positioned on at least one of the shoulder, the panel, and the base of the bottle.

31. The control system of claim 28 wherein the parison is molded to include a material distribution indicator that has a horizontal dimension of between about $2.5 \times 10^{-4}$ cm and $12.5 \times 10^{-2}$ cm, and a vertical dimension of between about $2.5 \times 10^{-4}$ cm and $2.5 \times 10^{-1}$ cm.

32. The control system of claim 28 wherein the parison thermal conditioning section is a re-heating section including a plurality of horizontally extending and vertically spaced infrared heater elements, and wherein
- the control feedback circuit is coupled to a supply of power to the heater elements to effect changes to the pattern of re-heating to which the parisons are subjected.

* * * * *

UNITED STATES PATENT AND TRADEMARK OFFICE
CERTIFICATE OF CORRECTION

PATENT NO.   : 6,620,352 B1
DATED        : September 16, 2003
INVENTOR(S)  : Craig Davis, Spencer Minton and Eddy Roberts It is certified that error appears in the above-identified patent and that said Letters Patent is hereby corrected as shown below:

Column 12,
Line 30, change "indicator" to -- indicator; (new paragraph) --

Column 14,
Lines 25 and 30, change "11" to -- 10 --

Column 16,
Line 28, change "modify" to -- modifying --
Line 43, change "containers; and" to -- containers; --

Signed and Sealed this

Twenty-third Day of December, 2003

JAMES E. ROGAN
*Director of the United States Patent and Trademark Office*